(12) United States Patent
Toporek

(10) Patent No.: US 11,672,914 B2
(45) Date of Patent: Jun. 13, 2023

(54) RFID DOSE TRACKING MECHANISM FOR INJECTION DEVICES

(71) Applicant: SANOFI, Paris (FR)

(72) Inventor: Maurice Toporek, Frankfurt am Main (DE)

(73) Assignee: Sanofi, Paris (FR)

( * ) Notice: Subject to any disclaimer, the term of this patent is extended or adjusted under 35 U.S.C. 154(b) by 446 days.

(21) Appl. No.: 16/954,394

(22) PCT Filed: Dec. 18, 2018

(86) PCT No.: PCT/EP2018/085395
§ 371 (c)(1),
(2) Date: Jun. 16, 2020

(87) PCT Pub. No.: WO2019/121616
PCT Pub. Date: Jun. 27, 2019

(65) Prior Publication Data
US 2021/0077735 A1 Mar. 18, 2021

(30) Foreign Application Priority Data

Dec. 21, 2017 (EP) ..................................... 17306864

(51) Int. Cl.
*A61M 5/315* (2006.01)
(52) U.S. Cl.
CPC ...... *A61M 5/3155* (2013.01); *A61M 5/31568* (2013.01); *A61M 2205/3553* (2013.01); *A61M 2205/581* (2013.01); *A61M 2205/582* (2013.01)
(58) Field of Classification Search
CPC ............ A61M 5/3155; A61M 5/31568; A61M 2205/3553; A61M 2205/581; A61M 2205/582
See application file for complete search history.

(56) References Cited

U.S. PATENT DOCUMENTS 6,482,185 B1 11/2002 Hartmann
7,935,088 B2 5/2011 Veasey et al.
(Continued)

FOREIGN PATENT DOCUMENTS

CN 104093438 10/2014
CN 104411349 3/2015
(Continued)

OTHER PUBLICATIONS

PCT International Preliminary Report on Patentability in International Appln. No. PCT/EP2018/085395, dated Jun. 23, 2020, 7 pages.
(Continued)

*Primary Examiner* — Dung T Ulsh
(74) *Attorney, Agent, or Firm* — Fish & Richardson P.C.

(57) ABSTRACT

Described is a dose tracking mechanism for a drug delivery device, including an RFID device with an electric circuit and a switch operable to open and close the electric circuit to transmit a wireless signal to a receiving device when the electric circuit is closed by the switch. The switch is configured to open and close in response to operation of a dose setting and/or a dose dispensing mechanism of the drug delivery device, and the closing and opening of the electric circuit generates a pulse of the wireless RFID signal. In one embodiment, each pulse corresponds to a unit of a dose of medicament set by the dose setting mechanism or dispensed by the dose dispensing mechanism from a drug container of the drug delivery device, depending on if the dose setting or dose dispensing mechanism is arranged to toggle the switch.

20 Claims, 6 Drawing Sheets

(56) References Cited

U.S. PATENT DOCUMENTS

| | | | |
|---|---|---|---|
| 2006/0175427 A1 | 8/2006 | Jonientz et al. | |
| 2008/0140018 A1 | 6/2008 | Enggaard et al. | |
| 2008/0243088 A1* | 10/2008 | Evans | A61B 90/98 604/246 |
| 2009/0318876 A1 | 12/2009 | Hansen et al. | |
| 2011/0270214 A1 | 11/2011 | Jorgensen et al. | |
| 2011/0319861 A1 | 12/2011 | Wilk | |
| 2012/0101451 A1 | 4/2012 | Boit et al. | |
| 2012/0232520 A1* | 9/2012 | Sloan | G01N 33/48792 604/504 |
| 2014/0276583 A1* | 9/2014 | Chen | A61M 5/31546 604/207 |
| 2015/0202375 A1 | 7/2015 | Schabbach et al. | |
| 2015/0302818 A1* | 10/2015 | Cowe | G09G 5/00 345/440.2 |
| 2015/0352281 A1 | 12/2015 | Pfrang | |
| 2016/0184597 A1 | 6/2016 | Andresen et al. | |
| 2016/0213856 A1 | 7/2016 | Despa et al. | |
| 2016/0259913 A1* | 9/2016 | Yu | A61M 5/31511 |
| 2017/0274149 A1 | 9/2017 | Aeschlimann | |

FOREIGN PATENT DOCUMENTS

| | | |
|---|---|---|
| CN | 105268057 | 1/2016 |
| CN | 106537126 | 3/2017 |
| CN | 107427641 | 12/2017 |
| EP | 0300552 | 1/1989 |
| EP | 2674181 | 12/2013 |
| EP | 3178507 | 6/2017 |
| JP | S64-86978 | 3/1989 |
| JP | 2017-529918 | 10/2017 |
| WO | WO 2013/076026 | 5/2013 |
| WO | WO 2013/098421 | 7/2013 |
| WO | WO 2013/177135 | 11/2013 |
| WO | WO 2014/111338 | 7/2014 |
| WO | WO 2016/019375 | 2/2016 |
| WO | WO 2016/038498 | 3/2016 |
| WO | WO 2016/131713 | 8/2016 |
| WO | WO 2016/155997 | 10/2016 |
| WO | WO 2017/011926 | 1/2017 |

OTHER PUBLICATIONS

PCT International Search Report and Written Opinion in International Appln. No. PCT/EP2018/085395, dated Feb. 19, 2019, 9 pages.

* cited by examiner

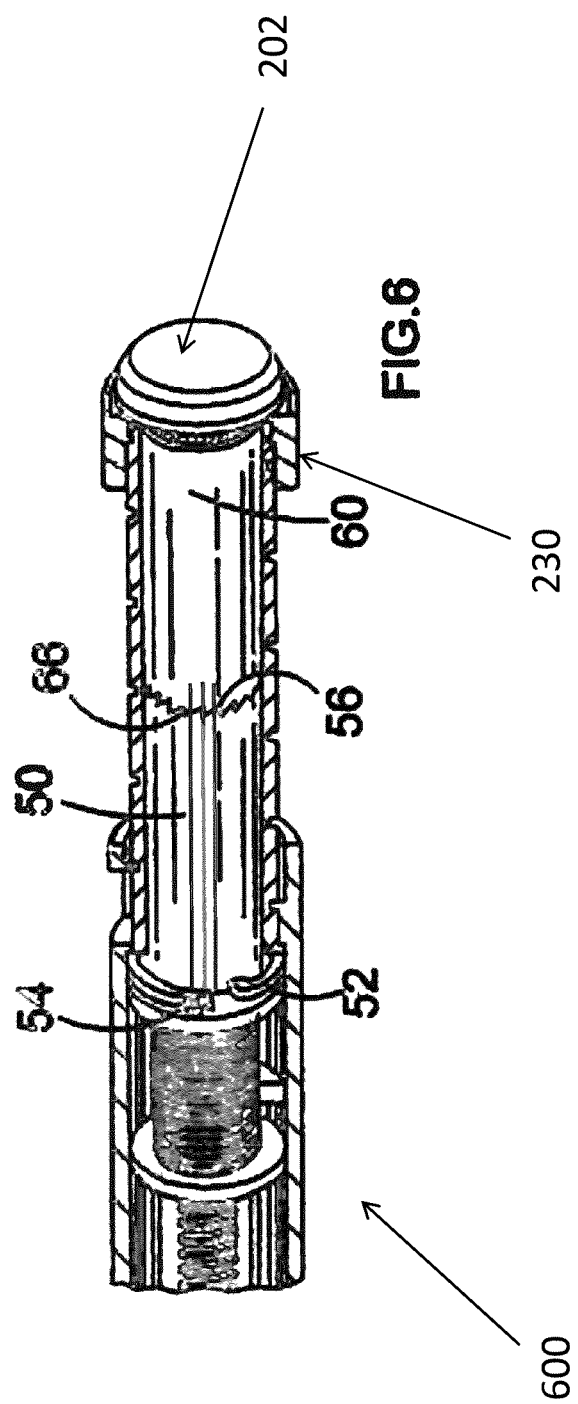

RFID DOSE TRACKING MECHANISM FOR INJECTION DEVICES

CROSS REFERENCE TO RELATED APPLICATIONS

The present application is the national stage entry of International Patent Application No. PCT/EP2018/085395, filed on Dec. 18, 2018, and claims priority to Application No. EP 17306864.4, filed on Dec. 21, 2017, the entire disclosures of which are incorporated herein by reference.

TECHNICAL FIELD

This disclosure relates to a dose tracking mechanism for generating pulses of an RFID signal to track the amount of a dose delivered from a drug delivery device.

BACKGROUND

A variety of diseases can be treated by injection of a medicament. Such injections can be performed using drug delivery devices, which can be applied either by medical personnel or by patients themselves. As an example, type-1 and type-2 diabetes can be treated by patients themselves by injection of drug doses, for example once or several times per day. For instance, a pre-filled disposable drug pen or autoinjector can be used as a drug delivery device. Alternatively, a re-usable pen or autoinjector may be used. A re-usable pen or autoinjector allows replacement of an empty medicament cartridge (or any other kind of medicament container) by a new one. Either type of pen or autoinjector may come with a set of one-way needles that are replaced before each use. The medicament dose may vary individually, therefore a user (e.g., a patient or health care professional) may select the amount of medicament required (e.g. dial a dose) by operating a dose setting mechanism of the drug delivery device prior to use.

SUMMARY

This disclosure relates to drug delivery devices having RFID electronics capable of being switched on and off (i.e., pulsed) in order to track a set or delivered dose of a medicament from the drug delivery device. This principle is based on using an RFID chip, which typically includes a memory and an antenna formed by an electric circuit. In operation, when the RFID chip is in the reach of a reader device such as a smart phone with an RFID reader, the antenna receives a signal from the smart phone and sends a wireless response signal according to the information encoded in the memory of the chip. In a representative example, the electric circuit of the antenna is open in a default state and is closed (e.g., completing the circuit and enabling the antenna to transmit the response signal) in synchronization with the movements of a dose setting or dispensing operating of the drug delivery device. In this manner, repetitive opening and closing of the RFID antenna results in a countably pulses of the wireless response signal (i.e., an RFID signal), which are synchronized such that the number of pulses indicates an amount of movement of a dose setting or dose dispensing mechanism of the drug delivery device. Where, for example, if 10 units of a medicament is delivered from a drug delivery device with a corresponding movement of a dose delivery mechanism, 10 pulses of the RFID signal are created. Aspects of this system can be implemented in a drug delivery device in a number of ways. In one example, a mechanical clicker is configured to operate the closing of the circuit of the antenna at each click, where a dose delivery mechanism is arranged to actuate the clicker during a dose delivery operation. Thus, the RFID signal is sent in a pulsed manner, where the number of pulses is proportional to the number of clicks, and where the mechanical clicker and dose delivery mechanism are arranged such that the number of clicks represents an amount of medicament that is dispensed. Finally, an external device counts the number of detected RFID pulses and computes the amount of medicament delivered during the dose dispensing operation.

In addition, a medicament and/or dose information can be transmitted with the encoded information of the RFID chip. In some instances, this may be only a unique tag serial number, or may be product-related information such as a stock number, lot or batch number, production date, or other specific information. Because RFID chips can have individual serial numbers, aspects of the present RFID tracking mechanism can discriminate among several tags that might be within the range of the RFID reader (i.e., an external device) and read several tags simultaneously. In this manner, it can be ensured that only the correct device is interrogated and the respective response is captured by the RFID reader.

Certain aspects of the present disclosure result in several advantages beyond the ability to easily track a set and/or dispensed dose from a drug delivery device. For example, a drug delivery device often includes a serial, stock, batch number, or production date in addition to information regarding the medicament, such as expiration, drug name, drug type, and concentration. Because an RFID chip is able to store specific data stored in a local memory, including any of the aforementioned information, and transmit this data in the RFID signal itself. This data can also be centrally tracked by the manufacturer to assist in recalls, track and analyze patient behavior, and monitor product usage. The use of a passive RFID chip has the advantage of being simple, reliable, and cost-effective. Additionally, with existing drug delivery devices, there are only minor modifications required to the dose delivery or setting mechanism to integrate the RFID chip, due to the small size and thickness of typical RFID chips. For example, an existing pen injector with a feedback clicker only needs to have an RFID chip and switch into the housing such that the switch in the electronic circuit that is operated by the existing feedback clicker. Optionally, the clicker itself can be modified to serve as a switch.

An example embodiment of the present disclosure is a drug delivery device having a dose tracking mechanism including a housing and an RFID device. The RFID device includes an electric circuit including an antenna and a switch operable to open and close the electric circuit, where the antenna is configured to transmit a wireless signal to a receiving device when the electric circuit is closed by the switch. The switch is configured to open and close in response to operation of a dose setting mechanism of the drug delivery device to set a dose of a medicament and/or a dose dispensing mechanism of the drug delivery device to dispense a dose of medicament. Closing and opening of the electric circuit generates a pulse of the wireless signal the pulse is usable to identify a quantity of medicament administered by the drug delivery device.

In some instances, the switch is configured to close and subsequently open the electric circuit periodically during a dose setting operation to set the dose and/or a dose dispensing operation to dispense to dose.

In some instances, each pulse corresponds to an amount of the medicament set by the dose setting mechanism and/or dispensed by the dose dispensing mechanism such that a total number of pulses indicates a total amount of the medicament.

In some instances, the switch is operationally coupled to a clicker mechanism, where the clicker mechanism is operated during the dose setting operation and/or the dose dispensing operation.

In some instances, the clicker mechanism includes a feedback mechanism configured to produce an audible or tactile feedback during the dose setting operation or the dose delivery operation, and where the switch arranged to be actuated by the feedback mechanism.

In some instances, the switch is integrally formed with the clicker mechanism.

In some instances, the dose setting mechanism or the dose dispensing mechanism includes a one or more actuation features configured to engage the switch of the RFID device in succession during the dose setting operation or the dose dispensing operation such that the switch closes and subsequently opens the electric circuit to generate one pulse for each of the one or more of actuation features that engaged the switch.

In some instances, the dose setting mechanism is configured to move proportionally to the dose set during the dose setting operation and/or the dose dispensing mechanism is configured to move proportionally to the dose dispensed during the dose dispensing operation, and where the one or more actuation features are configured to operate the switch such that the switch generates one pulse for each step of movement of the dose setting mechanism and/or the dose dispensing mechanism such that a number of the pulses indicates the amount of the dose set or dispensed.

In some instances, the dose setting mechanism includes a dose dial sleeve configured to rotate helically with respect to the housing.

In some instances, dose dial sleeve includes one or more actuation features configured to engage the switch, each of the one or more of actuation features corresponding to a set dose indicated by the dose dial sleeve during the dose setting operation.

In some instances, the dose dispensing mechanism includes a piston rod configured to move with respect to the housing during a dose dispensing operation, and where the dose dispensing mechanism includes the one or more actuation features configured to engage the switch, each of the one or more of actuation features corresponding to an amount of movement of the piston rod.

In some instances, the RFID device is a passive RFID device configured to transmit the wireless signal when RF energy is received from an external RFID reader.

In some instances, the dose tracking mechanism includes a power source, and where the RFID device is an active RFID device configured to receive power from the power source and to transmit the wireless signal using the received power when the switch closes the electric circuit.

In some instances, the wireless signal includes identification information related to the drug delivery device or a medicament contained therein.

Another example of the present disclosure is a method for wirelessly tracking an indication of a dose injected by a drug delivery device. The method includes opening and then closing an electric circuit of an RFID device once for each unit of movement of a dose dispensing mechanism of the drug delivery device during a dose dispensing operation or for each unit of movement of a dose setting mechanism of the drug delivery device during a dose setting operation by toggling a switch in the electric circuit and transmitting a pulse of a wireless signal via an antenna of the RFID device for each closing of the electric circuit, the RFID device transmitting a number of pulses proportional to a quantity of a dose of medicament set during the dose setting operation or dispensed during the dose dispensing operation.

In some instances, the wireless signal includes information a medicament delivered by the dose dispensing mechanism during the dose dispensing operation and/or the drug delivery device, where the information is sufficient to enable calculation of the amount of medicament that has been delivered by the drug delivery device based on the number of pulses transmitted.

In some instances, the method includes receiving an RF energy from an external device with the antenna of the electric circuit and transmitting the wireless signal with the antenna of the RFID device using the received RF energy.

In some instances, the method includes receiving electric energy from an internal power storage device with the RFID device when the electric circuit is closed and transmitting the wireless signal with the antenna of the RFID device using the received electric energy.

In some instances, the dose dial is a dose dial sleeve, and where moving the dose dial sleeve one unit for each unit of the dose including rotating the dose dial sleeve with respect to a housing of the drug delivery device.

In some instances, rotating the dose dial sleeve with respect to a housing of the drug delivery device including moving the dose dial sleeve helically with respect to the housing.

In some instances, moving the dose dial one unit includes engaging and disengaging an actuation feature of the dose dial with the switch to open and close the switch.

In some instances, the method includes producing an audible or tactile feedback for each unit of movement of the dose dial.

In some instances, the opening and the closing of the switch operating a feedback mechanism producing the audible or tactile feedback for each unit of movement of the dose dial.

In some instances, the wireless signal includes identification information related to the drug delivery device or a medicament contained therein.

In some instances, the RFID transmits the wireless signal at a first frequency in response to the movement of the dose dial, and the method includes opening and then closing a second switch of the electric circuit of the RFID device when a trigger button of the drug delivery device is activated and transmitting the wireless signal at a second frequency when the second switch closes the electric circuit.

Yet another example is a method for wirelessly transmitting an indication of a dose of a medicament delivered by a drug delivery device. The method includes moving a dose setting mechanism of the drug delivery device to set the dose, actuating a drug dispensing mechanism, the drug dispensing mechanism moving one unit for each unit of the dose, the moving of the dose dispensing mechanism opening and then closing a switch of an electric circuit of an RFID device once for each unit of movement of the dose dispensing mechanism, the RFID device transmitting a wireless signal when the electric circuit is closed such that the RFID device pulses the transmission of the wireless signal with a number of pulses equal to the units of the dose, receiving the indication of the dose by receiving and counting the pulses of the wireless signal from the RFID device with an external device, and deriving an amount of the medicament delivered by counting the number of pulses.

BRIEF DESCRIPTION OF THE FIGURES

FIG. 6 is an illustration of the clicker assembly of the drug delivery device.

DETAILED DESCRIPTION

Figure 1A:
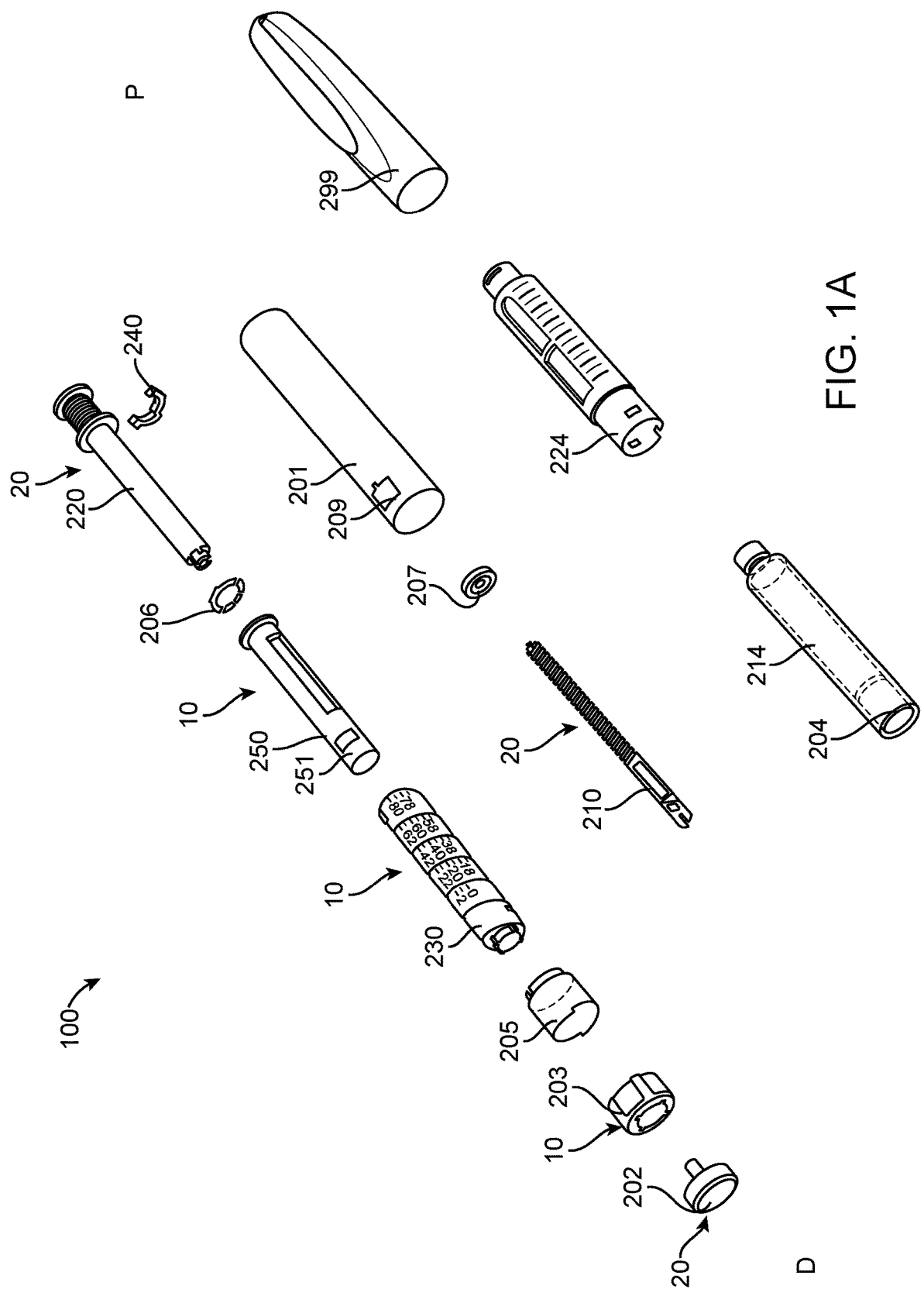
FIG. 1A is an exploded view of a drug delivery device.

Cartridge-based injection and medical syringe systems can include integrated electronics that enable detection of a dose set by the user, or a measurement of the medicament delivered by the device (e.g., a position sensor), along with some feature for presenting this information to the user. For example, a digital display arranged to display a dose or a wireless connection to transmit the dose data. However, the above examples typically require an internal source of power, either to run the sensor(s) or the wireless transmission. Certain aspects of the present disclosure provide a drug delivery device with a dose tracking mechanism generating a wireless RFID signal that encodes one or more of a dose set and a dose delivered by the drug delivery device without the need for an internal power source. Certain aspects also relate to a dose tracking mechanism that generates the wireless RFID signal using an active (e.g., battery powered) RFID transmitter. In certain aspects, a switch is provided in the drug delivery device to close a close a circuit of an RFID chip, such that the dose tracking mechanism transmits a pulse of an RFID signal each time the circuit closes. In some example, the switch is provided as an addition component of a drug delivery device. In another example, the switch is operated by a clicker or feedback mechanism of the drug delivery device. In yet another example, the switch in integrated into the clicker or feedback mechanism.

In a representative embodiment, an RFID circuit in a drug delivery device includes a switch that opens and closes multiple times during the movement of a dose setting operation or a dose delivery operation. Each closing of the switch completes the RFID circuit such that the RFID circuit is able to transmit a wireless signal in response to a received signal only with the switch closing the circuit. In operation, the received signal is transmitted from some external device, such as a smart phone or an RFID reader, and the RFID circuit of the drug delivery device transmits a pulse of the RFID signal each time the switch closes the RFID circuit. In this manner, for example, during a drug delivery operation, a dose dispensing mechanism moves an amount corresponding to the amount of medicament delivered. During this movement, the dose dispending mechanism repeatedly actuates the switch, which closes the RFID circuit a number of times corresponding to the amount of medicament delivered. Finally, because this closing of the switch completes the RFID circuit, a number of pulses of the RFID signal are generated (in response to a received signal during the dose delivery operation). The number of pulses are then easily counted by an external device, and the amount of medicament delivered is determined based on a known relationship between the movement of the dose dispensing mechanism (e.g., the number of pulses) and an amount of medicament delivered for each pulse. In an alternative configuration, the switch is nominally closed, and opens during the dose dispensing or dose setting operation such that pulses generated are the inverse of the earlier configuration, and there resultant gaps in the signal are counted to determine the amount of medicament delivered, or the dose set.

While the above description includes a passive RFID system (i.e., no internal power source), passive RFID signals are often limited in this transmission distance. Alternatively, an active RFID chip could be used, where active RFID chips are generally understood to require a source of power beyond any received RF energy in order to generate the wireless response signal with more power. The design is similar in function compared to the above passive system, with the addition of a battery to boost the transmission power of the RFID signal. The power is only required to feed the system when in use. In some examples, an air-zinc battery is used to ensure that the drug delivery device is disposable, if necessary. In this instance, the air-zinc battery is arranged such that a protective latch is removed automatically when using the drug delivery device the first time at dial up. In some instances, the battery is located in the dose release button and the latch is fixed to a pen housing. Then the RFID chip is ready, but does not initially transmit the RFID signal, as the circuit is open in default state, as mentioned above. In some instances, the switch is integrated with an existing clicker that provides a tactile or audible feedback of the operation, and, during a dose dispense operation, the switch is closed synchronously to the clicker noise, and thus the RFID signal is pulsed. In the active RFID system, similar to the passive system, an external device counts the number of pulses and computes the amount of medicament from that. In some instances, the actual data that is being sent from the RFID chip in the wireless signal comprises information on the medicament/device and this can be by the reader to interpret the data. For example, the external device can assign the captured number of pulses to the "right" device and store it appropriately in a separate storage for this device/medicament.

FIG. 1A is an exploded view of a drug delivery device 100, which may be a disposable or reusable drug delivery device. The drug delivery device 100 includes a housing 201, covered by a replaceable cap 299, where the housing 201 contains a cartridge 214 and a cartridge housing 224 in which the cartridge 214 is disposed. A stopper 204 is disposed in the body of the cartridge 214 and can be advanced within the cartridge 214 during use to expel medicament from the cartridge 214. A needle assembly can be affixed to the cartridge housing 224 or the cartridge 114 to deliver the medicament. To drive the stopper 204 into the cartridge 214, the drug delivery device 100 includes a piston rod 210, a drive sleeve 220, and a trigger button 202 (e.g., a dose dispensing mechanism 20), which act together to drive a pressure plate 207 against the stopper 204 and into the cartridge 214. A medicament or drug dose to be ejected from the drug delivery device 100 is selected by turning a dosage knob 203, which is connected by a threaded insert 205 a dose dial sleeve 230, where rotation of the dose dial sleeve 230 by the dosage knob 203 causes the selected dose to be displayed in a dosage window 209 in the housing 201 and causes a clicker 250 to interact with the drive sleeve 220 via a spring clutch 206. Together, the dosage knob 203, dose dial sleeve 230, and clicker 250 are a dose setting mechanism 10. The dose dial sleeve 230 is arranged around a clicker 250, which includes a feedback mechanism 251 that generates a tactile or audible feedback with rotation of the dose dial sleeve 230. The clicker 250 is coupled to the drive sleeve 220 with a metal clutch spring 206, and a last dose nut 240 is provided on the drive sleeve 220. The last dose nut 240 advances with each dose dispensing operation to track the total medicament remaining in the cartridge 214. Finally, an injection button 202 is included, and depression injection button 202 activates a dose dispensing operation of the drug delivery device 100.

While the dose setting mechanism 10 is illustrated as the dosage knob 203, dose dial sleeve 230, and the clicker 250, as described above, one skilled in the art will appreciate that any number of different dose setting mechanisms are route in the art for the purposes of setting a dose of a drug delivery device and aspects of the present disclosure are compatible with other such dose setting mechanisms. Similarly, while the dose dispensing mechanism 20 is illustrated as a includes the piston rod 210, drive sleeve 220, trigger button 202, one skilled in the art will appreciate that any number of different dose dispensing mechanisms (e.g., drive mechanisms) are route in the art for the purposes of delivering or dispensing a dose of a drug delivery device and aspects of the present disclosure are compatible with other such dose dispensing mechanisms.

Continuing with the operation of the drug delivery device 100, turning the dosage knob 203 causes a mechanical click sound to provide acoustical feedback to a user by rotating the dose dial sleeve 230 with respect to the clicker 250. The numbers displayed in the dosage display 209 are printed on the dose dial sleeve 230 that is contained in the housing 201 and mechanically interacts with the drive sleeve 220 via the metal spring clutch 206 to interact with the cartridge 114. When the injection button 202 is pushed, the drug dose displayed in the display 209 will be ejected from the drug delivery device 100. During a dose setting operation, the drive sleeve is helically rotated with the dose dial sleeve 230 in the distal direction D. When the injection button 202 is pushed, the drive sleeve 220 is released and advanced proximally, which causes rotation of the piston rod 210. The rotation of the piston rod 210 drives the pressure plate 207 against the stopper 204 of the cartridge 214, which drives the stopper 204 into the cartridge 214 to expel the medicament from the cartridge 214. A more detailed description of a representative drug delivery device is described in U.S. Pat. No. 7,935,088 B2, which is incorporated herein by reference.

Figure 1B:
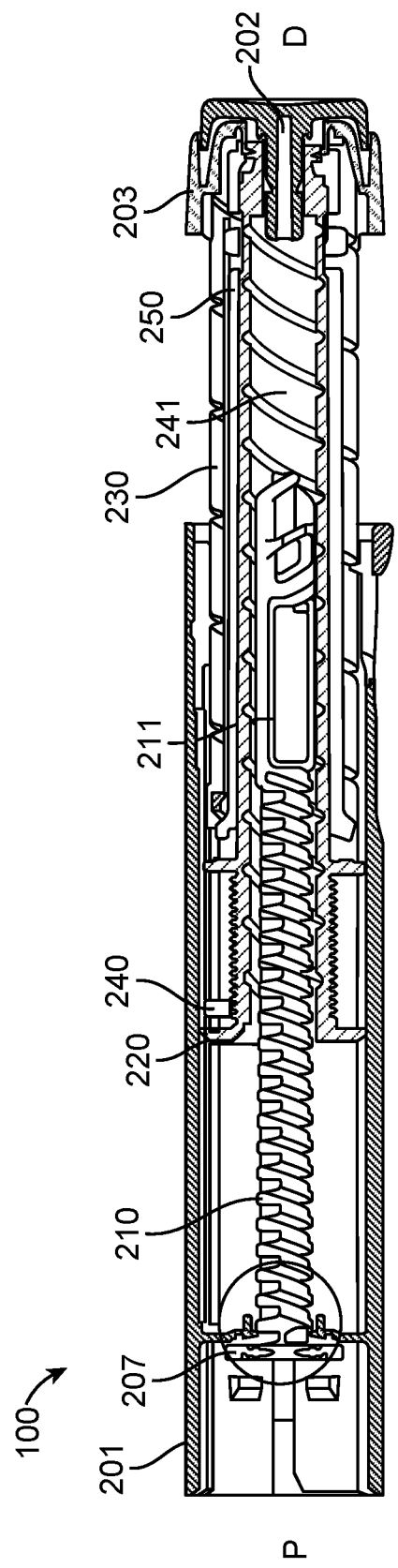
FIG. 1B is a cross sectional view of a portion of the drug delivery device of FIG. 1A.

FIG. 1B is a cross sectional view of a portion of the drug delivery device 100 of FIG. 1A. FIG. 1B shows the drug delivery device 100 at the end of a dose setting operation and prior to a dose dispensing operation, where the dose dial sleeve 230 and the drive sleeve 220 have been helically rotated with respect to the housing 201 and a threaded end 211 of the piston rod 210 to set the dose. The last dose nut 240 is shown advanced along the drive sleeve 220 from an initial position. Upon activation of the injection button 202, the drive sleeve advances into the housing 201, and a set of inner threads 241 induce rotation of the piston rod 210. Rotation of the piston 210 drives the piston rod 210 and the pressure plate 207 proximally to drive the stopper 204 into the cartridge 214 (FIG. 1A).

Figure 2A:
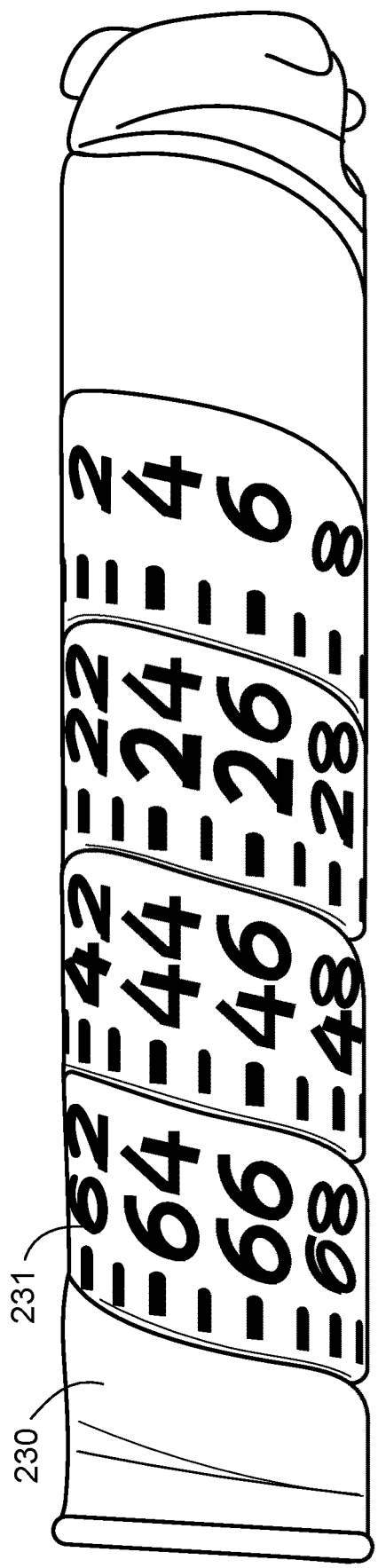
FIGS. 2A and 2B are illustration of a dose dial sleeve and clicker, respectively.
Figure 2B:
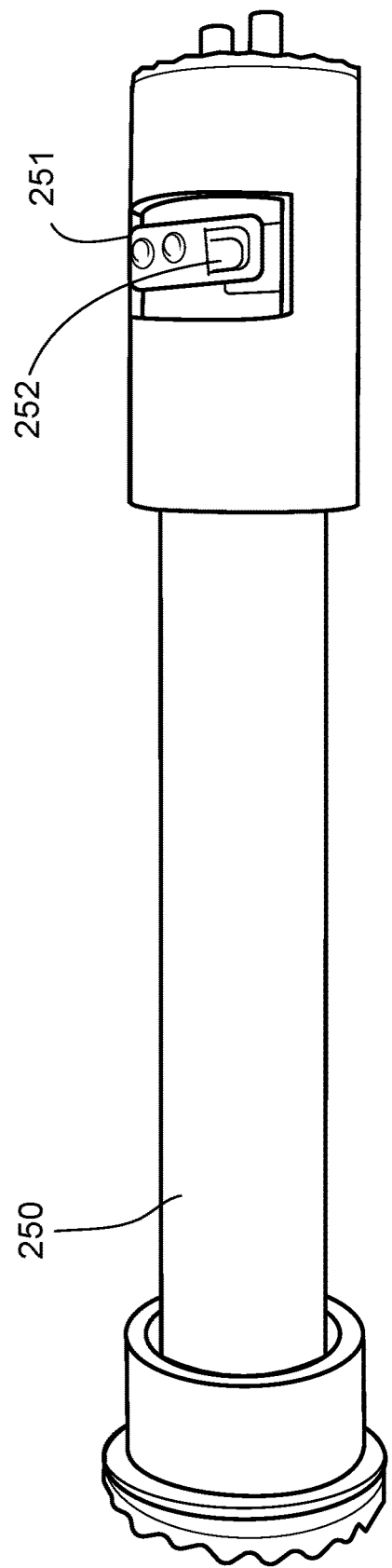

FIGS. 2A and 2B are illustration of a dose dial sleeve and clicker, respectively. FIG. 2A shows the helical outer thread of the dose dial sleeve 230, and FIG. 2B shows the clicker 250 and feedback mechanism 251, where feedback mechanism 251 includes a resilient arm 252 configured to be deformed periodically during a dose dispensing operation of the drug delivery device 100, such that the resilient arm produces a click upon returning to a non-deformed state. The feedback mechanism is, in some instances, a dispense clicker configured to be moved over ribs or splines disposed on an inner surface of the dial sleeve 230 during a dose delivery operation. The clicker 250 is, in some instances, a dose setting clicker, having teeth disposed on the proximal ends of the clicker 250, which are configured to engage the metal spring 206 during a dose setting operation (e.g., the action when selecting a dose size before actually injecting the medicament). In some instances, the metal spring 206 has two splines that engage with ribs at the inner surface of housing part 201 to prevent spring 206 from rotating against housing part 201. When setting a dose, sleeves 230 and 250 rotate unison and as the metal spring 206 does not rotate teeth move over the splines of the metal spring 206 and produce a click sound. In one example, as shown in U.S. Pat. No. 7,935,088, an inner surface of the housing 201 includes splines configured to deflect the resilient arm 252 as the clicker mechanism 250 rotates with respect to the housing 201.

Figure 3:
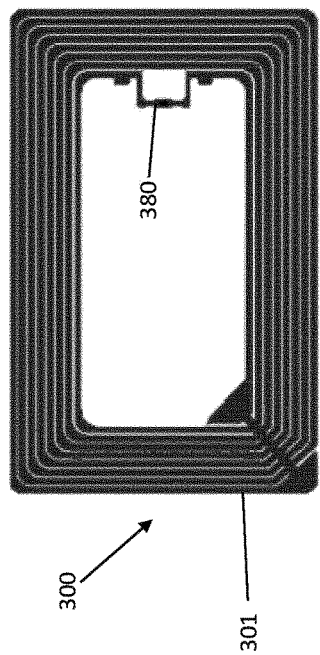
FIG. 3 is an illustration of an RFID circuit.

FIG. 3 is an illustration of a passive a RFID circuit 300, which may be a printed RFID circuit. The RFID circuit includes an RFID chip 380 and an antenna 301, where the antenna is coiled around the RFID circuit 300. In operation, the antenna 301 absorbs an incoming wireless reader signal from an external device and forms a weak magnetic field, which creates a current in the antenna to provide power to the RFID chip 380. The RFID chip 380 includes a memory, which stores, for example, information related to the drug delivery device 100 or a medicament contained therein. Upon power being provided to the RFID chip 380, the RFID generates a response signal in the antenna 301, which transmits the information from the RFID chip's 380 memory as a wireless signal. This wireless signal can be received by the external device that sent the reader signal, or by another device close by.

Figure 4:
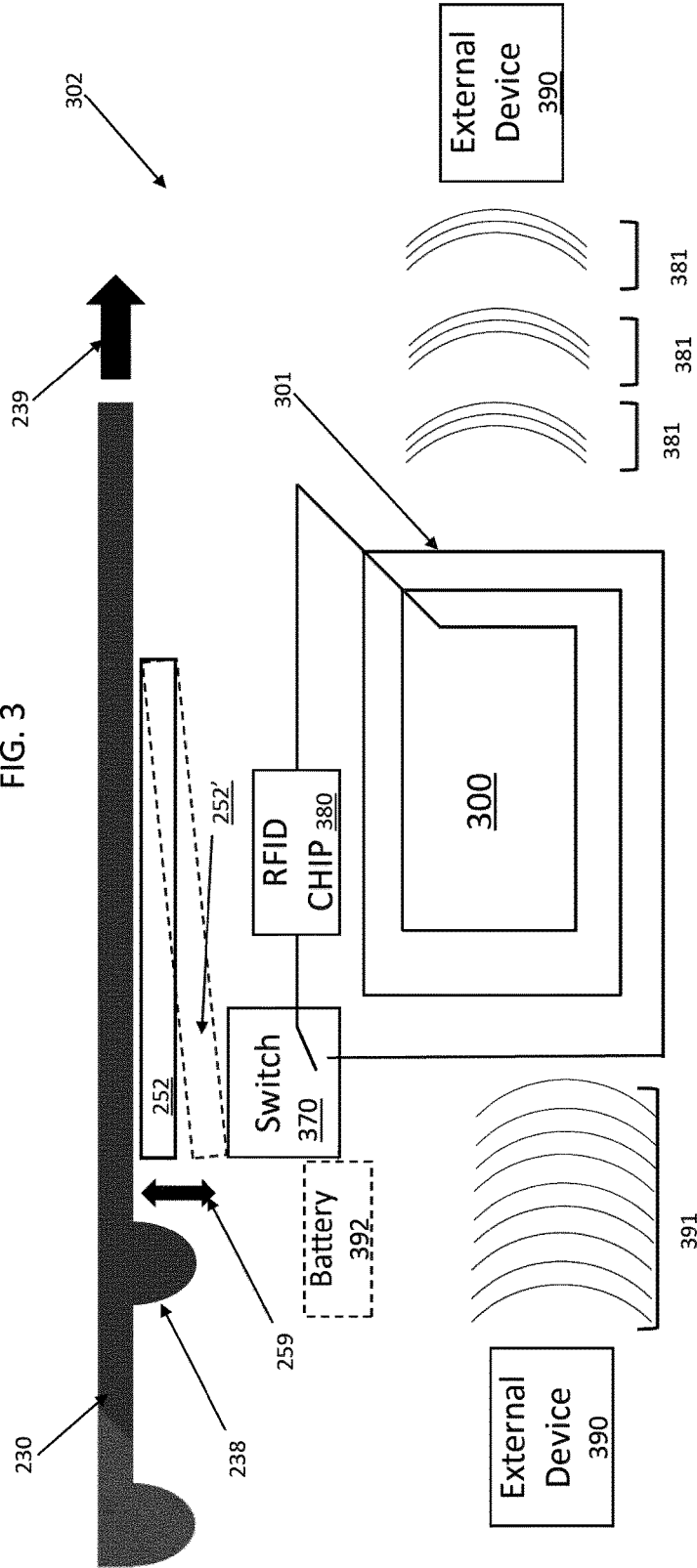
FIG. 4 is a schematic of the operation of a switched RFID electronic circuit.

FIG. 4 is a schematic of the operation of a RFID dose tracking mechanism 302 in the drug delivery device 100 further comprising a dose tracking assembly with an RFID device and a switch configured to open and close the circuitry of the RFID device. The switch is configured to open and close while the dose setting and/or dose dispensing mechanism is operated. The RFID dose tracking mechanism 302 includes a RFID circuit 300, a switch 370 in the RFID circuit 300, and a resilient arm 252 arranged to engage the switch 370 during operation of the drug delivery device 100. In some instances, the RFID dose tracking mechanism 302 includes a battery 392 configured to provide power to the RFID circuit 300 when the switch 370 is engaged, but as described above, the RFID dose tracking mechanism 302 can also be a passive RFID system, and FIG. 4 shows an external device 390 providing a wireless reader signal 391 to the antenna 301 of the RFID circuit in order to generate power for the RFID chip 380.

In operation, either passive or active, a mechanism of the drug delivery device 100 is configured to operate the switch 370 during a dose setting operation or a dose dispensing operation. For example, FIG. 4 shows a portion of the dose dial sleeve 230 having actuation features 238 that engage the resilient arm 252 of the clicker during a dose setting operation (which is shown as movement of the dose dial sleeve in the direction of arrow 239). Similarly, a component of the dose dispensing mechanism (e.g., the drive sleeve 220) could have actuation features arranged to engage the switch 370 during a dose delivery operation. In both cases, movement of the dose dispensing mechanism or dose setting mechanism 10 causes the actuation features 238 to engage the resilient arm 252 and deflect it (e.g., position 252') to operate the switch 370 once as each actuation feature passes across the resilient arm 252. The dose setting and/or the dispensing action may involve rotational movement; alternatively, linear movement of a component of the drug delivery device 100 may also be used to operate the switch.

The switch 370 is configured to open and close the RFID circuit 300, specifically the antenna 301, such that, with the switch 370 open, the antenna 310 does not receive the reader signal 391 or provide power from the battery 392 to the RFID chip 380. In some instances, the battery 392 is a zinc-air battery. Similarly, with the switch 370 open, the antenna 301 does not transmit the response signal 381.

The switch 370 and the RFID antenna 301 are electrically connected via wires. The RFID circuit 300 could be placed on a housing component, preferably as a label (plastic, paper, adhesive RFID chip). Alternatively, the RFID circuit 300 could be located inside the housing 201, for example, at the inner surface of the injection button 202 or between injection button 202 and another inner component such as the dose dial sleeve 230.

Generally speaking, the switch 370 registers operation of the mechanism (e.g., during a dial and/or dispense operation) and correlates this to modulate the RFID response signal 381. The modulation is a pulse of, detectable by the external device 390 as, for example, amplitude modulation of a signal at a specific frequency. When the switch 370 is closed, the RFID circuit 301 is completed and the response signal 381 is transmitted, which indicates that one toggling of the switch 370 occurred, and the actuation features 238 can be configured to generate one pulse of the response signal 381 for any amount of medicament. The number of pulses of the response signal 381 is proportional to the amount of medicament that has been dispensed when the resilient arm 252 is actuated by the dose dispensing mechanism. In a more complicated example, the number of pulses can also be correlated to the dose that has been dialed or set. However, in this example, the drug delivery device includes a mechanism that can distinguish between up and down dialing and must "know" when a setting operation is ended (e.g., by sensing the start of the dose dispensing operation).

In an alternative dose tracking mechanism 302 configuration, the switch 370 is arranged to be contacted or operated by contact by any adjacent components of the drug delivery device 100 that move relative to one another during operation (dose setting and/or dose dispensing). For example, movement between the dose dial knob 203 and housing 201, between the dose dial sleeve 230 and the window 209, or between the dose dial sleeve 230 and the housing 201. Additionally, more than one clicker mechanism 250 may be present, where one is arranged for triggering during the dose setting operation, and another is arranged for triggering during the dose dispensing operation.

Figure 5:
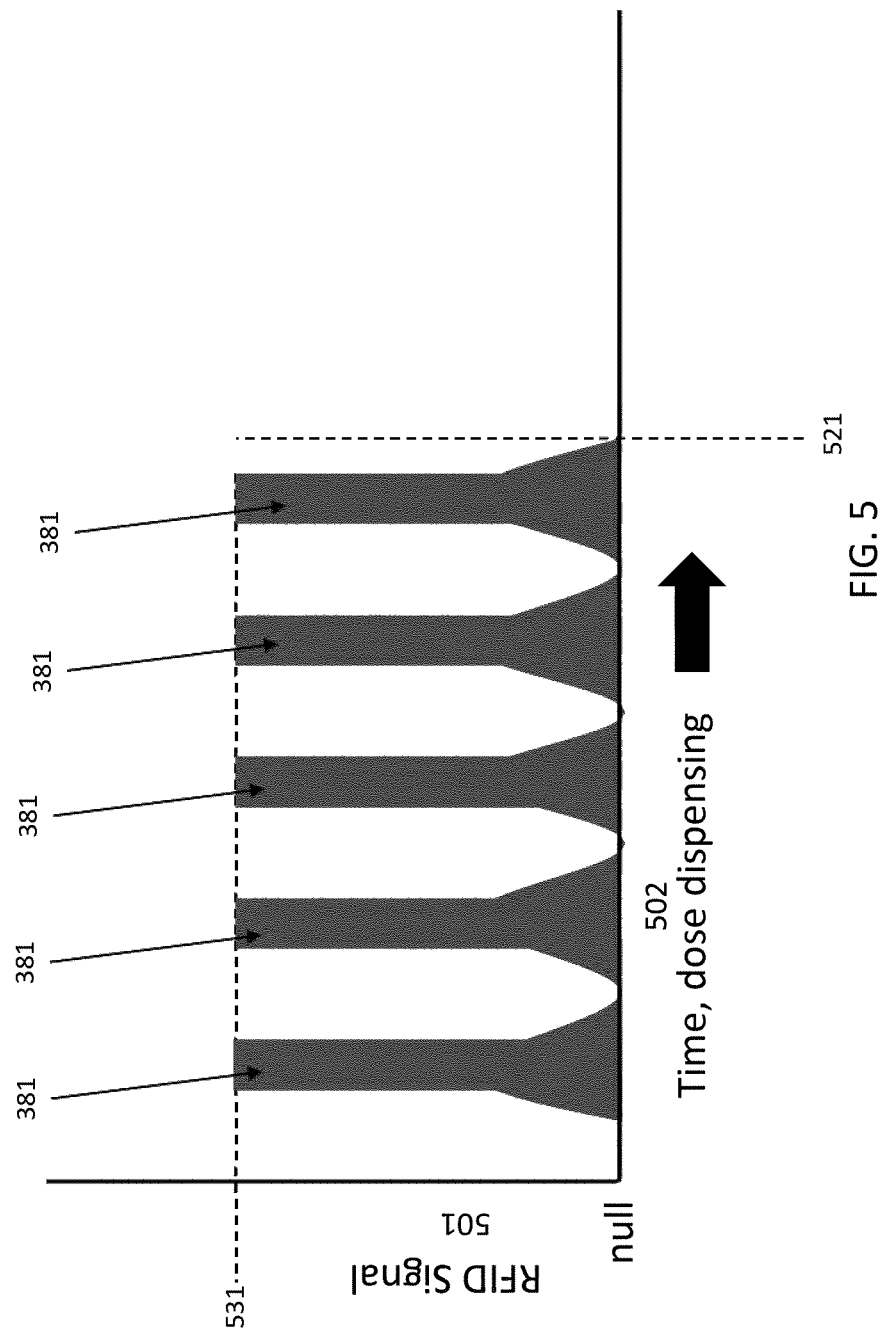
FIG. 5 is a graph of the RFID signal over time during a dose dispensing operation.

FIG. 5 is a graph of the strength 501 of the RFID response signal over 381 time 502 during a dose dispensing operation of a drug delivery device 100 having the dose tracking mechanism 302. FIG. 5 shows the RFID response signal 381 has an approximately square-wave pattern during dose dispensing operation, where each pulse of the response signal 380 corresponds to a time when the switch 370 is closed periodically by actuation features 238 on a component of a dose dispensing mechanism.

Each pulse of the response signal 380 has approximately amplitude 531, and each pulse of the response signal 380 includes the information stored in the RFID chip 380. The pulses of the response signal 380 continue until the end of the dose dispensing operation, at time 521, where 5 pulses of the response signal 380 has occurred. In some instances, each pulse of the response signal 380 represents a predefined amount of the medicament dispensed from the drug delivery device 100 by the dose dispensing mechanism.

FIG. 6 is an illustration of a clicker cylinder assembly of a drug delivery device 600. FIG. 6 shows another design of the dose tracking mechanism, using electrically conductive components. In FIG. 6, a two-part clicker cylinder 50, 60 is made from an electrically conducting material or alternatively coated with such a material, e.g., copper, nickel, silver, or gold. The two-part clicker cylinder 50, 60 includes an inner cylinder 50 and an outer cylinder 60. The outer cylinder 60 includes a clicker arm 52 that run along the outer surface of inner cylinder 50, wherein inner cylinder 50 has ribs or splines. Alternatively, the inner cylinder 50 has teeth on its outer surface that run across a resilient rib or arm producing a click sound. Continuing to refer to FIG. 5, a toothed member 54 of the clicker arm 52 is also furnished as electrically conducting element, and the clicker arm 52 runs along the outer surface of the clicker cylinder 50. When the clicker cylinder 50 rotates relative to the clicker arm 52, click sounds are generated. For each clicker arm 52, a particularly toothed member 54 runs along an inclined surface of a longitudinal spline 56 and the falls down in a trough between the splines 56, making a click sound. During each fall, there is no contact between toothed member 54 and cylinder 50 and thus an electrical contact between the two-part clicker cylinder 50, 60 is interrupted. An RFID circuit 300 is in electrical connection with the two-part clicker cylinder 50, 60 and interrupting the contact leads to opening the circuit of the RFID chip 380 and thus the RFID response signal 381 is pulsed.

In some instances, the clicker arm 52 could additionally be configured as a switch 370. For example, the tip (outer surface) of toothed member 54 could comprise a dome switch, where the dome switch is closed when the toothed member 54 runs across the top of the splines 56 of outer surface of cylinder 50. Alternatively, the inner surface of toothed member 54 could comprise a dome switch. The dome switch is closed when the toothed member 54 is pushed radially inwards and about a surface before crossing the top of a spline 56. In other instances, the abutting surface (e.g., inner surface of housing 201) carries a dome switch, which is activated upon the toothed member being forced radially outward towards the housing 201 when moving across each spline 56.

Aspects of the systems disclose above enable medical injectors to employ 'smart' technologies by way of an attached of the included electronic components (e.g. RFID, sensor) to give a certain features to a cartridge of a drug delivery device (e.g. of a pen-type injector). When integrating electronics into drug delivery device, a one or more components may be active (e.g., a sensor to measure certain properties of the injector or cartridge) and require an energy source, which typically could be a battery. One alternative is to use a means of energy harvesting as a power source replacement for a battery.

Embodiments of the present disclosure can also apply to prefilled single and double chamber syringes that may not use a cartridge. In some instances, the dose tracking mechanism is contained in the cartridge or in the drug delivery device in a manner enabling the dose tracking mechanism assembly to sense a change in the fill level of the cartridge or syringe after an injection. In some instances, components of the electronics assembly are located outside of the cartridge or in different parts of the cartridge or drug delivery device.

Some of the features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described embodiments by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package, cartridge, or "drug container" adapted for use with a drug delivery device. The drug container may be, for example, a cartridge, syringe, reservoir, or other vessel configured to provide a suitable chamber for storage (e.g., short- or long-term storage) of one or more pharmaceutically active compounds. For example, in some embodiments, the chamber may be designed to store a drug for at least one day (e.g., 1 to at least 30 days). In some embodiments, the chamber may be designed to store a drug for about 1 month to about 2 years. Storage may occur at room temperature (e.g., about 20° C.), or refrigerated temperatures (e.g., from about −4° C. to about 4° C.). In some embodiments, the drug container may be or may include a dual-chamber cartridge configured to store two or more components of a drug formulation (e.g., a drug and a diluent, or two different types of drugs) separately, one in each chamber. In such embodiments, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance that is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N- lithocholyl-gamma-glutamyl)-des(B30) human insulin; B29-N-(ω-carboxyheptadecanoyl)-des(B30) human insulin and B29-N-(w-carboxyhepta-decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-114, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

The term "drug delivery device" according to instant disclosure shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. In some instances, the drug delivery device is of the injector-type.

The term "housing" according to instant disclosure shall preferably mean any exterior housing ("main housing", "body", "shell") or interior housing ("insert", "inner body") having a helical thread. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

A number of embodiments of the present disclosure have been described. Nevertheless, it will be understood that various modifications may be made without departing from the spirit and scope of the present disclosure. Accordingly, other embodiments are within the scope of the following claims.

The invention claimed is:

1. A dose tracking mechanism for use in a drug delivery device, comprising:
    a housing; and
    an RFID device comprising:
        an electric circuit comprising an antenna, and
        a switch operable to open and close the electric circuit, wherein the antenna is configured to transmit a wireless signal to a receiving device when the electric circuit is closed by the switch,
    wherein the switch is configured to open and close in response to operation of at least one of (i) a dose setting mechanism of the drug delivery device to set a dose of a medicament, or (ii) a dose dispensing mechanism of the drug delivery device to dispense a dose of medicament,
    wherein at least one of a closing or an opening of the electric circuit generates a pulse of the wireless signal, and
    wherein the switch is configured to close and subsequently to open the electric circuit periodically during at least one of a dose setting operation to set the dose or a dose dispensing operation to dispense the dose,
    wherein the switch is operationally coupled to a clicker mechanism having a feedback mechanism and configured to be operated during at least one of the dose setting operation or the dose dispensing operation, the switch being arranged to be actuated by the feedback mechanism, and
    wherein each pulse corresponds to at least one of (i) an amount of the medicament set by the dose setting mechanism or (ii) an amount of the medicament dispensed by the dose dispensing mechanism such that a total number of pulses indicates a total amount of medicament.

2. The dose tracking mechanism of claim 1, wherein the feedback mechanism is configured to produce an audible or tactile feedback during the dose setting operation or the dose dispensing operation.

3. The dose tracking mechanism of claim 1, wherein the switch is integrally formed with the clicker mechanism.

4. The dose tracking mechanism of claim 1, wherein the dose setting mechanism or the dose dispensing mechanism comprises one or more actuation features configured to engage the feedback mechanism to actuate the switch of the RFID device in succession during the dose setting operation or the dose dispensing operation such that the switch closes and subsequently opens the electric circuit to generate one pulse for each of the one or more actuation features that engaged the feedback mechanism.

5. The dose tracking mechanism of claim 4, wherein the dose setting mechanism is configured to move proportionally to the dose set during the dose setting operation and/or the dose dispensing mechanism is configured to move proportionally to the dose dispensed during the dose dispensing operation, and wherein the one or more actuation features are configured to operate the switch such that the switch generates one pulse for each step of movement of the dose setting mechanism and/or the dose dispensing mechanism such that a number of the pulses indicates the amount of the dose set or dispensed.

6. The dose tracking mechanism of claim 4, wherein the dose setting mechanism comprises a dose dial sleeve configured to rotate helically with respect to the housing.

7. The dose tracking mechanism of claim 6, wherein the dose dial sleeve comprises at least one actuation feature configured to engage the switch, each of the at least one actuation feature corresponding to a set dose indicated by the dose dial sleeve during the dose setting operation.

8. The dose tracking mechanism of claim 1, wherein the dose dispensing mechanism comprises a piston rod configured to move with respect to the housing during the dose dispensing operation, and wherein the dose dispensing mechanism comprises one or more actuation features configured to engage the switch, each of the one or more actuation features corresponding to an amount of movement of the piston rod.

9. The dose tracking mechanism of claim 1, wherein the RFID device is a passive RFID device configured to transmit the wireless signal when RF energy is received from an external RFID reader.

10. The dose tracking mechanism of claim 1, comprising a power source, and wherein the RFID device is an active RFID device configured to receive power from the power source and to transmit the wireless signal using the received power when the switch closes the electric circuit.

11. The dose tracking mechanism of claim 1, wherein the wireless signal comprises identification information related to the drug delivery device or the medicament contained therein.

12. A method for wirelessly tracking an indication of a dose injected by a drug delivery device, the method comprising:
    actuating a switch to periodically open and then close an electric circuit of an RFID device during a dose dispensing operation or during a dose setting operation of the drug delivery device, wherein the dose setting operation is to set a dose and the dose dispensing operation is to dispense the dose,
    wherein the switch is operationally coupled to a clicker mechanism having a feedback mechanism, and is actuated by the feedback mechanism, and wherein closing and opening of the electric circuit causes generation of one or more pulses, each pulse being generated by at least one of the closing or the opening of the electric circuit and corresponding to at least one of (i) an amount of a medicament set in the dose setting operation or (ii) an amount of the medicament dispensed in the dose dispensing operation such that a total number of the one or more pulses indicates a total number of medicament; and transmitting the one or more pulses via an antenna of the RFID device, wherein each of the one or more pulses is transmitted as a wireless signal when the electric circuit is closed.

13. The method of claim 12, further comprising:
receiving an RF energy from an external device with the antenna of the electric circuit; and
transmitting the wireless signal with the antenna of the RFID device using the received RF energy.

14. The method of claim 12, further comprising:
receiving electric energy from an internal power storage device with the RFID device when the electric circuit is closed; and
transmitting the wireless signal with the antenna of the RFID device using the received electric energy.

15. The method of claim 12, further comprising:
producing an audible or tactile feedback during the dose setting operation or the dose dispensing operation.

16. The method of claim 12, wherein transmitting the pulse of the wireless signal comprises transmitting the pulse of the wireless signal at a first frequency, and wherein the method further comprises:
opening and then closing a second switch of the electric circuit of the RFID device when a trigger button of the drug delivery device is activated and transmitting the wireless signal at a second frequency when the second switch closes the electric circuit.

17. The method of claim 12, further comprising moving a dose dial sleeve one unit for each unit of the dose during the dose setting operation.

18. The method of claim 17, wherein moving the dose dial sleeve one unit for each unit of the dose comprises rotating the dose dial sleeve with respect to a housing of the drug delivery device.

19. The method of claim 18, wherein rotating the dose dial sleeve with respect to the housing of the drug delivery device comprises moving the dose dial sleeve helically with respect to the housing.

20. A method for wirelessly transmitting an indication of a dose of a medicament delivered by a drug delivery device, the method comprising:
moving a dose setting mechanism of the drug delivery device to set the dose;
actuating a dose dispensing mechanism, the dose dispensing mechanism moving one unit for each unit of the dose, the moving of the dose dispensing mechanism causing a clicker mechanism of the drug delivery device to periodically open and then close a switch of an electric circuit of an RFID device, wherein closing and opening the electric circuit causes generation of one or more pulses, each pulse being generated by at least one of the closing or the opening of the electric circuit such that a total number of the one or more pulses indicates a total units of the dose;
transmitting, by the RFID device, a wireless signal for each pulse in the one or more pulses when the electric circuit is closed;
receiving, by an external device, the pulses of wireless signal received from the RFID device; and
deriving an amount of the medicament delivered by counting the number of pulses received.

* * * * *